United States Patent [19]

Heyser

[11] 4,279,019
[45] Jul. 14, 1981

[54] METHOD AND APPARATUS FOR DELAY ANALYSIS OF ENERGY TRANSMITTED THROUGH A MEDIUM

[75] Inventor: Richard C. Heyser, Tujunga, Calif.

[73] Assignee: California Institute of Technology, Pasadena, Calif.

[21] Appl. No.: 39,154

[22] Filed: May 15, 1979

[51] Int. Cl.³ .................. G06F 15/20; G01S 9/23
[52] U.S. Cl. .................. 364/569; 364/506; 364/553; 367/102
[58] Field of Search ............ 364/506, 553, 569; 367/8, 13, 102; 343/5 SA, 5 FT

[56] References Cited

U.S. PATENT DOCUMENTS

| | | | |
|---|---|---|---|
| 3,135,942 | 6/1964 | Tucker et al. | 367/102 |
| 3,466,652 | 9/1969 | Heyser | 367/102 X |
| 3,798,590 | 3/1974 | Jacobson et al. | 367/102 X |
| 3,906,213 | 9/1975 | Meriaux et al. | 364/569 |

Primary Examiner—Jerry Smith
Attorney, Agent, or Firm—Freilich, Hornbaker, Wasserman, Rosen & Fernandez

[57] ABSTRACT

A method and apparatus is disclosed for determining the manner by which an initial injection of wave energy is modified by a medium under test using a time delay spectrometer (TDS) and a fast Fourier transform (FFT). A switch allows either the time delay spectrum or an energy-time curve to be displayed. A differentiator at the input of the FFT corrects for inverse square loss of energy through the medium, i.e., compensates for spherical expansion of energy. Different arrangements of the TDS adapt the system to a medium having variable time delay, or adapt the system for measurement of harmonic distortion through the medium.

24 Claims, 4 Drawing Figures

METHOD AND APPARATUS FOR DELAY ANALYSIS OF ENERGY TRANSMITTED THROUGH A MEDIUM

BACKGROUND OF THE INVENTION

This invention relates to apparatus and method for determining the manner by which an initial injection of signal energy is modified by a medium under test to a response state that is manifest as a redistribution of that energy.

There is for each event a defined scalar entity called total energy, E. The way in which this total energy is expressed in terms of the state variables, s, of an observation is called total energy density, E(s).

Energy density is a departure from equilibrium of those aspects of an event which are capable of doing work. It is composed of two parts: (1) that part representing the instantaneous configuration of work producing elements; and (2) that part representing the transformation that is in process in those work producing elements. The first part may be called potential energy density and designated V(s). The second part may be called kinetic energy density and designated T(s). Total energy density is thus given by the equation $$E(s) = V(s) + T(s).$$

It is, and must be, a property of those partitions in energy density that their net sums are ultimately equal, i.e., that $$\Sigma_s V(s) = \Sigma_s T(s)$$

Any manifestation of energy density, expressed in a frame of reference, will be proportional to the square of some observable expressed in that frame of reference.

There exists a unique relationship between V(s) and T(s) such that if $$E = \int_s E(s)ds < \infty,$$

and if there is some f(s) and g(s) such that $$f^2(s) = V(s)$$

$$g^2(s) = T(s);$$

Then f(s) and g(s) are related by the Hilbert transform, and there is always a complex number $$h(s) = f(s) + ig(s),$$

where $i = \sqrt{-1}$
such that $$|h|^2(s) = |E(s)|.$$

Every linear observation is sufficiently described as a complex number h(s).

The expression of energy density and of its partitioning into potential and kinetic parts is what may be called the energy-coordinate expression, where the coordinate is one chosen. For example, if a frequency coordinate is chosen the term is energy-frequency, and if a time coordinate is used, the term becomes energy-time.

Although there can be many methods of expression, it is preferred that the energy-time, or energy-frequency, consist of two parts: (1) an amplitude, expressed in decibels or nepers, and (2) a phase, expressed in degrees or radians. Linear circuit theory already uses an expression coinciding with the energy-frequency expression. The power spectrum of a signal is proportional to the magnitude part, and the phase spectrum is proportional to the phase part. Thus, conventional frequency response is expressed as an amplitude in dB and a phase angle is energy-frequency.

The concept of energy-time, while mathematically straight forward, and physically meaningful, requires a realignment of conventional thinking. This is because we have been taught to think of frequency response as a complex measurement value, but time response as a scalar measurement value. But note that in a measurement in terms of just potential energy density, the value observed is indeed scalar. The imaginary part, kinetic energy density is nevertheless present and is treated in any mathematical treatment of the observed value as a Hilbert transform. For example, note that expressions involving energy are always present in mathematical processes involving the observed value, and more complete expressions involve both in-phase and quadrature components. Also note that cosine as well as sine terms are needed for general Fourier expansions. Thus, to bring scalar observations into alignment with the energy theorem, it is necessary that these characteristics of a Hilbert transform be present, except in calculations of simple time or frequency.

The inventor has disclosed in U.S. Pat. No. 3,466,652 a new measurement technique which can be used to break away from traditional time or frequency measurements. That technique produces what may be called a time delay spectrum. It is, in fact, a measurement technique which breaks away from the conventional time-frequency coordinates. That type measurement is in itself useful. However, one of the economically useful things which it can do for engineers and scientists is make conventional time-frequency measurements under physical conditions which would make more conventional techniques awkward. For example, making an echoic frequency measurement in an otherwise noisy and reverberant environment is virtually impossible with conventional techniques. Signals sent out from a single source of sound can reflect, refract and bounce many times before arriving at the measurement location. Thus the net sound measured is composed of a multiplicity of patterns arriving at different times and possessing different spectral properties. The classic frequency response from such a reverberation set is the steady state sinewave response in which all sound arrivals are combined into one grand spectrum. But often it is desirable to know what the spectrum would be for a particular sound following a particular path as though sound from the other signal paths were not present. The technique described in the aforesaid patent for such a particular path measurement is called time delay spectrometry (TDS).

The signal used in TDS has a constant total energy density and a uniquely defined partition into potential and kinetic energy densities. In the time domain, this signal takes the form $$h(t) = e^{i\phi(t)} = \cos\phi(t) + i\sin\phi(t)$$

It is a property of this TDS signal that, when applied to a system under test, it illicits a response that is a mathematical hologram. However, unlike the more restricted class of optical hologram more familiar to all persons, the TDS hologram can alter dimensionality.

In an abstract sense, applying the TDS technique to a radiation signal of a system creates a response which is a hologram of the conventional response of that system. This holographic form is the function of the TDS processing for effectively slicing out of the system response only those things that are of interest. Those things can then be recorded in a form that has significance to the desired measurement. For example, applying the simple quadratic phase chirp $$e^{i\frac{1}{2}ax^2}$$

to a system will illicit a response that, in and of itself, has no significance in terms of the normal time domain response of that nework. In the case of a sound system, the response sounds like a complicated chirping of birds. To a listener, the sound is thus totally unintelligible because it is a hologram. The hologram has the property that is a two-dimensional representation involving the parameters of (1) time relative to the instant of stimulation, and (2) rate of change in phase. This representation can be made on a delay plane, i.e., two dimensional plane on which one dimension (coordinate) is time delay, and the other is the phase rate of the energy response of a transducer (e.g., microphone) at a point of interest in space remote from the signal source (e.g., speaker).

A tracking filter process can isolate all signals with a fixed time delay and produce a modified hologram that can be further processed for either (1) a smoothed frequency spectrum (energy density) of signals bearing a predetermined time delay between the source and transducer along a path of interest, which may be a direct path or a reflected path or (2) the time delay energy density of signals occupying a predetermined frequency band. It is because of this modality that the term "time delay spectrometry" is used.

TDS can use any constant total energy density phasoid $$e^{i\phi(x)}$$

It is not limited to the quadratic phase chirp cited above for an example. However, certain circuit and/or algorithm simplicities result from the use of a quadratic chirp if the information desired is the impulse response or the Fourier transform of the impulse response. Consider a system that operates on a signal s(t) with a function f(t) to produce a response r(t), as follows:

$$r(t) = s(t) \otimes f(t)$$

where ⊗ is the convolution operator. The system may be thought of as mapping the signal properties to the response space. The response is the image of the signal under the influence of the system.

An optical holograph is formed on photographic film as an interference pattern between a coherent illuminating wave used as a reference and the diffraction pattern of the object being photographed. In the same manner, an electronic hologram may be formed by the interference between a coherent signal from a source and the response of a system to that signal.

Converting an optical hologram to a scene in the original coordinate system requires coherent illumination of the hologram with the reference wave, and observation of stationary wavefront combinations. Similarly, stimulating an electronic hologram with coherent waves and summing the net behavior can convert the electronic hologram to the time coordinate called energy-time, or the frequency coordinate called energy-frequency.

Although reference will frequently be made hereafter to the sound field, it is ultimately the intent of every physical measurement to determine the manner by which an initial injection of signal energy is modified by a system under test to a response state that is manifest as a redistribution of that energy, either in the time or frequency domain, i.e., either in energy and time or energy and frequency coordinates discussed hereinbefore. In particular, the measurement of the energy of response as a function of the time coordinate is hereafter referred to as the energy-time measurement. A plot of this response will be referred to hereinafter as the energy-time curve (ETC). Energy is plotted as the ordinate, and time as the abscissa, in a Cartesian coordinate system, but that choice is one of convenience only. Any other two dimensional plotting system may be used. Consequently, the description of preferred embodiments which follow with reference to an ETC in the conventional Cartesian coordinate system is by way of example, and not limitation.

Within the framework of the foregoing general discussion of TDS as it will be applied to an ETC, it should be recognized that an ETC will consist of two parts, (1) the logarithmic magnitude as a function of time, expressed either in decibels or nepers, and phase angle as a function of time expressed either in radians or degrees of rotation. Thus, the entity from which these energy terms derive has the form of a complex signal representation having a real (or in phase) term and an imaginary (or quadrature) term. In classic linear theory, where there is total expression of the signal, this complex entity is called the analytic signal which takes the form $$h(t) = f(t) + ig(t)$$

where $i = \sqrt{-1}$, f(t) is the real part called impulse response, and i(g)t is the imaginary part related to the real part by the mathematical relationship known as the Hilbert transform.

Determination of the ETC is of value in establishing the time-delay properties of complicated systems, such as architectural acoustics where sound from a source will reach a point through many different paths, and therefore with many different time delays. TDS, as described in the aforesaid U.S. Pat. No. 3,466,652 makes possible in-place measurement of architectural acoustic response for any frequency band of interest which possesses a selected fixed time delay between the loudspeaker excitation and acoustic perception at a microphone as disclosed in that patent. The technique of TDS is applicable to many other complicated systems, and to other forms of radiation, such as electromagnetic radiation (radar or laser radiation, for example). Consequently, reference to wave radiation hereinafter should be construed to mean any wave radiation and not simply sound of a loudspeaker through the air, although that has been the primary field of application for TDS since at least Apt. 30, 1971 when the inventor presented a paper to the 40th Convention of the Audio Engineering Society, Los Angeles published in three parts in Journal of the Audio Engineering Society, (1971) Volume 19, Number 9, (Part 1, December, pp 734–743; Part II November, pp 829–834; Part III pp 902–905).

A technique by which ETC could be determined is described in Part I of that paper at pages 741 and 742. But such a technique, and other contemporary methods are extremely lengthy and complicated. An object of this invention is to provide frequency sweeping arrangements for TDS which invert the role of time delay and frequency: time delay appears in terms of frequency, and frequency components appear in terms of time delays. A further object of this invention is to provide a technique for quickly obtaining an ETC using a frequency-sweeping arrangement for TDS.

SUMMARY OF THE INVENTION

In accordance with the present invention time delay spectroscopy (TDS) is employed with a test stimulus which varies in frequency with time such that the response, at a desired point of test, occupies a desired band of frequency for which a test is to be performed. The intercepted signal is passed through a tracking filter centered at all times on the desired received signal. The output of the tracking filter contains the arrival time information of the signal components in the form of frequency offsets, thus inverting the role of time delay and frequency offset. (Time delay appears in terms of frequency, and frequency components appear in terms of time delays.) This output may be passed through a narrow bandpass filter, in which case amplitude and phase information is in the frequency domain, but what is more important is that if this output is passed through a fast fourier transform (FFT) means, the magnitude and phase of the FFT means will constitute an energy-time curve. An alternative arrangement uses a differentiator at the input of the FFT means to correct for effects of range between the transmitter and receiver, i.e., to correct for inverse square loss (spherical spreading loss).

The novel features of the invention are set forth with particularity in the appended claims. The invention will best be understood from the following description when read in conjunction with the accompanying drawings.

DESCRIPTION OF PREFERRED EMBODIMENTS

Figure 1:
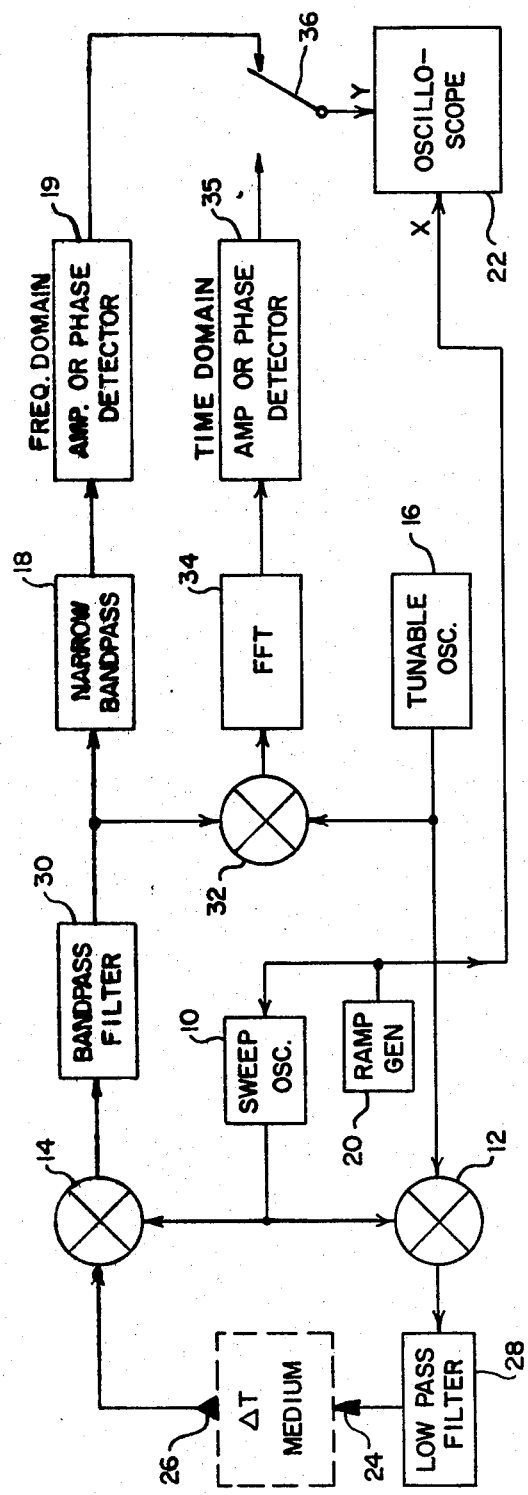
FIG. 1 is a block diagram of a time delay spectrometer in a new arrangement for measurement of energy density as a function of time.

FIG. 1 illustrates a time delay spectrometer (TDS) of the basic configuration shown in the aforesaid patent, but in a new arrangement. The basic TDS is comprised of a precision sweep oscillator 10, mixers 12 and 14, a tunable oscillator 16 and a narrow bandpass filter 18. A ramp generator 20 produces a voltage signal having a constant slope to sweep the oscillator 10, and to drive the horizontal sweep circuit of an oscilloscope 22 for display of the time delay spectrum of energy transmitted from a transmitter 24 through a medium with some fixed delay $\Delta T$ to a receiver 26. The transmitter may be a speaker, for example, and the receiver an appropriately matched transducer, such as a microphone in the case of a speaker for the transmitter. However, the transmitter and receiver could be chosen for any other type of energy wave transmission through the medium.

The output of the sweep oscillator is delivered to the mixer 12 where it is modulated by the output of the tunable oscillator which produces an offset frequency. The modulation process in the mixer produces the sum and difference of the signals thus mixed. A filter 28 passes only the difference for transmission. At the receiver, the mixer 14 receives the sweep frequency for modulation with the received signal. The sum and difference frequencies are then transmitted through a bandpass filter 30, and either the sum or difference is transmitted through the narrow bandpass filter 18 as the IF to be displayed as a function of time on the oscilloscope. The tunable oscillator permits this time delay spectrometer to look at the transmitted signal which passes through different paths through the medium and is therefore subject to different delay. To see what signal modification is produced by a particular path of some time delay, the tunable oscillator is adjusted. That effectively displaces the spectrum displayed in time.

The output of the tunable oscillator is applied to a mixer 32 which effectively cancels the offset to produce a signal for processing through means 34 for a fast Fourier transform (FFT) that produces a signal representative of total energy as a function of time for display on the oscilloscope as an energy-time curve (ETC). A switch 36 is provided to selectively display the amplitude, or phase, of the output of the FFT or the output of the narrow bandpass filter 18. The choice of amplitude or phase is made in the design of detectors 19 and 35. While the switch is in the position shown, data in the frequency domain is displayed as a TDS, and while in the alternate position, data in the time domain is displayed as an ETC.

It should be noted that a filter is not required to select one of the two frequencies (sum or difference) out of the mixer 32 because the FFT will, in the course of processing the signal, make the selection. Virtually any commercially available FFT may be used. It is assumed that the input section includes an analog to digital converter for digital processing, and the output section includes a digital to analog converter. If a FFT is selected without these analog to digital and digital to analog converters, it would be a simple task to provide the converters synchronized to operate with the FFT.

Figure 2:
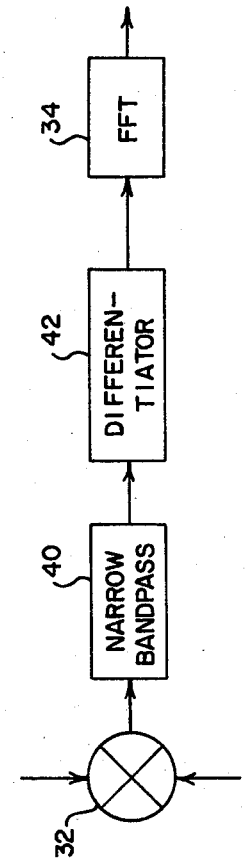
FIG. 2 illustrates a modification for the arrangement of FIG. 1.

In an alternative arrangement shown in FIG. 2 a narrow bandpass filter 40 is used to select the sum or difference signal out of the mixer 32 in order for an analog differentiator 42 to be used for preprocessing the signal into the FFT. This allows amplitude and phase to be displayed in the time domain with correction for inverse square loss in the medium through which the signal is transmitted from the transmitter 24 to the receiver 26.

Figure 3:
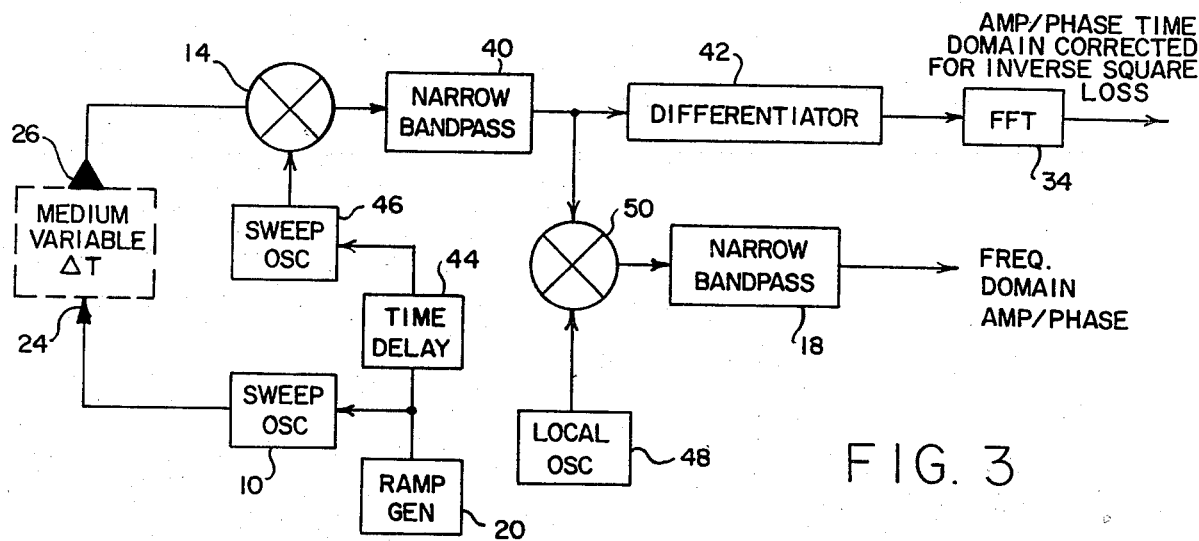
FIG. 3 illustrates an alternative arrangement of a time delay spectrometer for measurement of energy density as a function of time.

The arrangements of FIGS. 1 and 2 assume a medium having some uniform transmission delay, $\Delta T$. The arrangement for TDS shown in FIG. 3 is useful when the medium has a dispersive and/or time varying time delay, i.e., when $\Delta T$ is some function of frequency and/or time. Consequently, in this arrangement, a time delay element 44 having appropriate time delay properties is interposed between the ramp generator 20 and a second sweep oscillator 46. (Components which exactly correspond in function to components in FIG. 1 are referred to by the same reference numerals to facilitate understanding the variations in this arrangement.) Only mixer 14 is required in this arrangement because a tunable oscillator for an offset frequency is not used since the medium is assumed to have a non-constant time delay. The output of the mixer 14 is applied directly to the narrow bandpass filter 40 for processing in the FFT means 34 with a differentiator 42 to compensate for spherical expansion of the wave front i.e., to correct for inverse square law as an option in the manner described with reference to FIG. 2. A fixed local oscillator 48 and mixer 50 are provided as a frequency up converter into the narrow bandpass filter 18 for amplitude and/or phase display in the frequency domain.

Figure 4:
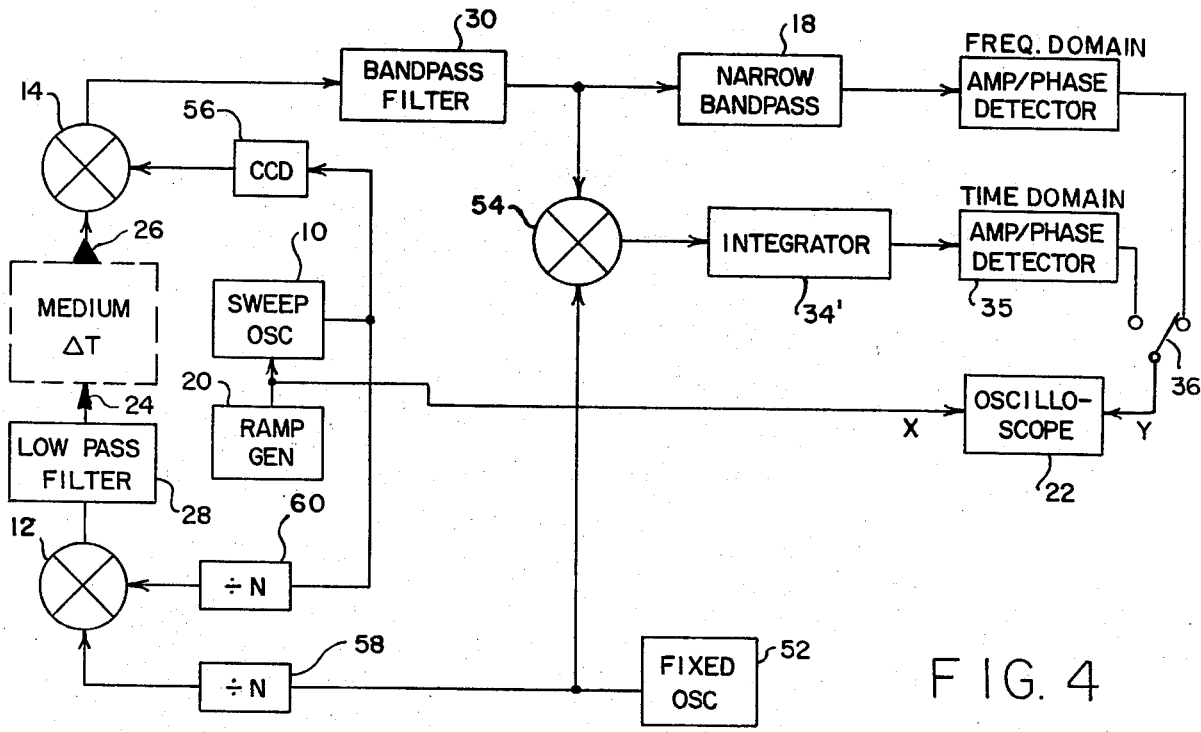
FIG. 4 illustrates yet another arrangement to allow controlled time delay in the arrangement of FIG. 3, and to allow studying the delay time through a medium as a function of harmonic frequency response.

FIG. 4 is another arrangement that assumes a time delay through the medium between the transmitter 24 and receiver 26. It is thus very much like the arrangement of FIG. 1, but with an analog intergrator 34' replacing the FFT to display amplitude or phase in the time domain. The narrow bandpass filter 18 is used to display amplitude or phase in the frequency domain. A fixed oscillator 52 is used much as in the arrangement of FIG. 3 with a mixer 54, as an up converter. What is unique about this arrangement is in two parts, either of which, or both of which can be used. One part involves a programmable charge coupled delay (CCD) 56 performing much the same function as the time delay 44 in FIG. 3, but with the facility to change the delay for adjustment to the time delay of the medium. The other more significant part involves two programmable divide-by-N circuits 58 and 60 to shift the frequency of measurement progressively up from the fundamental (when N=1) to the second, third and higher harmonics. When N=1, the arrangement will sweep in frequency the signal transmitted through the medium, as in the arrangement of FIG. 1. When N=2, the difference frequency out of the mixer increases to produce the second harmonic of the signal first transmitted. When N is increased to 3, the third harmonic is produced by the mixer through the filter 18. The result is that the TDS or ETC characteristics of the medium may be studied as a function of harmonic frequency.

Examples of how these arrangements can be used to advantage will now be described. The arrangement of FIG. 1 may be used to determine the detailed nature of both the time and frequency domain characteristics of reverberation in an enclosure, such as an auditorium. If, as in the case of sound in air, the speed of propagation is essentially independent of frequency, then the sweep oscillator 10 may have an essentially linear progression of frequency with time. The tunable oscillator 16 is then used to convert the frequency of the oscillator 10 to the desired frequency range to be transmitted by the transducer 24 (a speaker). At the same time, the output of the tunable oscillator is applied to the mixer 32 to present a net signal to the FFT which is always a constant for a constant time delay $\Delta T$. Thus, the oscillator 16 may be adjusted so that the desired time delay signal component lies within the passband of filter 18, allowing extraction of this signal to the selective exclusion of signals of different time delays for subsequent demodulation and display. A demodulator is assumed to be present at the output of the bandpass filter 18 for this purpose. The mixer 32 compliments the offset created by the oscillator 16 such that the FFT input is a steady tone (constant frequency) for each value of time delay regardless of the frequency of the oscillator 16. Amplitude or phase in the time domain can then be selected for display through switch 16. The interaction of oscillators 10 and 16 through mixers 12 and 32 is such that the attribute of time delay $\Delta T$ in the medium is now presented as a frequency offset. The time and frequency domains are essentially swapped, as seen by the FFT. Normal action of the FFT then produces a display which may be directly an energy-time curve (ETC) display which may be directly interpreted as energy density as a function of time.

Desirable auditorium properties, such as reverberation time, may thus be readily determined from the ETC. One application of the arrangement in FIG. 1 is thus the ready determination of reverberation properties in an enclosure. Another is the sound (or other wave propagation) reflection properties of boundaries. If the signal from transmitter 24 passes into a medium and is reflected by some boundary to the receiver, then the ETC allows determination of length of time, $\Delta T$, between transmission and reception, and determination of reflection coefficients, both the amplitude and phase, of the reflecting boundary.

If the propagation from transmitter 24 is essentially spherical, as sound in air or water will be from a projector, then the modification in the arrangement of FIG. 1 shown in FIG. 2 corrects for the deleterious effects which spherical spreading of the propagated waves would otherwise have on the determination of reflection properties of objects at various distances from the transmitting transducer 24 and reception of wave energy at the transducer 26. One application of this modification is the creation of a sonar or radar which is self correcting for the loss of energy due to spherical wavefront expansion, and which has the additional capacity of time domain measurements of the reflection properties of boundaries or objects.

If the time delay between transmission of energy at the transducer 24, and reception of energy at the transducer 26, varies in time or in frequency, then the arrangement of FIG. 3 can be used to remove, or reduce, the effect which this may have on a measurement. One application is that of a high acuity sonar in which the output of the FFT is used to display range information. The time delay 44 is used to correct not only for gross time delay to and from the target but also for doppler and acceleration changes of the target. Another application is the measurement of seismic propogation through soil, in which the wave velocity is dependent upon wavelength. Elastic body waves which propogate through solids consist of compressional as well as shear waves which differ not only in average speed but also in wavelength-dependent speeds. The arrangement of FIG. 3 may be used for a more complete measurement of such seismic properties than now possible with conventional means.

Another application of FIG. 3 is the determination of the onset and decay of acoustic waves created by the application of high energy electromagnetic energy. For this application, sweep oscillator 10 and transmitter 24 are of one modality, electromagnetic, while receiver 26 is of another modality, acoustic. Opto-acoustic measurement is a powerful testing method now coming into prominence in materials testing. Time delay 44 is, in this application, that delay used to measure or compensate for mode conversion and relaxation effects. The ETC is then a significant display of energy decay of stimulated emission.

The arrangement of FIG. 4 may be used to determine the harmonic distortion properties of a device, such as loudspeakers, while operating in a reverberant environment. The ETC obtained may be used to determine the onset and direction of distortion components relative to the time of application of the fundamental signals giving rise to those distortion products.

Although the arrangement of FIG. 4 is used to detect the ETC of harmonic distortion components, it is clear that other products of interaction between the medium and transducers 24 and 26, such as cross-modulation products and harmonic terms, may similarly be detected and measured for their ETC. Still other applications will occur to those skilled in the art for this and other arrangements disclosed herein, even with some obvious modifications. It is therefore intended that the claims be interpreted to cover such applications and modifications.

What is claimed is:

1. A method for determining the manner by which wave energy is modified by a medium comprising the steps of transmitting through said medium wave energy which is swept in frequency over a predetermined range of interest, detecting said wave energy received through said medium at a remote point to obtain an output electrical signal which varies in frequency in a manner corresponding to the sweep of said wave energy, but delayed in time by an amount corresponding to the time delay of transmission through said medium, where said time delay may be zero, providing a generated signal swept in frequency in a manner corresponding to the sweep of said wave energy, but offset in time by an amount corresponding to the time delay of transmission of a particular path through said medium, where said particular path through said medium may be a direct, zero-time-delay path, and mixing said swept signal with said output electrical signal developed from energy waves detected, thereby to produce an IF signal for analysis in the frequency domain, and performing a further operation on the IF signal over the entire frequency spectrum of interest to produce a signal for display of amplitude or phase in the time domain.

2. A method as defined in claim 1 wherein said further operation comprises performing a fast Fourier transform operation on the IF signal over the entire frequency spectrum of interest to produce a signal representative of total energy as a function of time during which said transmitted wave is swept for display as an energy-time curve.

3. A method as defined in claim 2 wherein a path of interest through said medium has a uniform time delay, and wherein said wave energy is produced through a transducer by a generated electrical signal swept in frequency, including the step of mixing said generated electrical signal with a second signal of a frequency selected to produce a signal to be transmitted that is offset in frequency from said swept generated electrical signal sufficiently to offset said uniform time delay, thereby effectively displacing the frequecy spectrum of said IF signal in time, and including the step of mixing said second signal with said IF signal to cancel said offset in said IF signal prior to said further operation.

4. A method as defined in claim 3 including the step of differentiating the IF signal prior to performing the fast Fourier transform operation in order to correct the energy-time curve data for inverse square loss in the medium due to spherical expansion of the wave energy transmitted through said medium.

5. A method as defined in claim 4 including the steps of selecting the sum or difference frequency in the signal produced by mixing the second signal with said IF to produce a second IF signal and using an analog differentiator for the second IF signal.

6. A method as defined in claim 2 wherein a path of interest has a time delay that varies as a function of frequency or time, or a function of frequency and time, and said wave energy is produced through a transducer by a generated electrical signal swept in frequency over a predetermined time interval, and including the step of delaying said swept generated signal to produce said IF signal delayed in time a period corresponding to time delay of energy wave transmission through said medium.

7. A method as defined in claim 6 including the further step of mixing said IF signal with a signal from a local oscillator in an up converter for analysis in the frequency domain.

8. A method as defined in claim 6 or 7 including a further step of differentiating said IF signal prior to performing the fast Fourier transform operation in order to correct the energy-time curve data for inverse square loss in the medium due to spherical expansion of the wave energy transmitted through said medium.

9. A method as defined in claim 1 wherein said further operation comprises mixing said IF signal with a fixed frequency for up conversion, and integrating the higher frequency signal to display amplitude or phase in the time domain.

10. A method as defined in claim 1 or 9 wherein a path of interest through said medium has a uniform time delay, and wherein said wave energy is produced through a transducer by a generated electrical signal swept in frequency, including a further step of mixing with said generated electrical signal a second signal of a frequency selected to produce a signal to be transmitted that is offset in frequency from said swept electrical signal sufficiently to offset said uniform time delay, thereby effectively displacing the frequency spectrum of said IF signal in time, and mixing said second signal with said IF signal to cancel said offset in said IF signal prior to said further operation.

11. A method as defined in claim 10 wherein said signal to be transmitted is generated by mixing said generated electrical signal swept in frequency with said second signal through frequency dividers to divide equally the signals mixed by whole integers of 1, 2, 3 . . . N in order to produce said IF signal for analysis in the frequency domain and in the time domain as a function of harmonic frequency.

12. Apparatus for determining the manner by which wave energy is modified by a medium comprising means for transmitting through said medium wave energy which is swept in frequency over a predetermined range of interest, means for detecting said wave energy received through said medium at a remote point to obtain an electrical signal which varies in frequency in a manner corresponding to the sweep of said wave energy, but delayed in time by an amount corresponding to the time delay of transmission through said medium, where said time delay may be zero, means for providing a generated signal swept in frequency in a manner corresponding to the sweep of said wave energy, but offset in time by an amount corresponding to the time delay of transmission of a particular path through said medium, where said particular path through said medium may be a direct zero time delay path, and mixing said swept signal with said electrical signal developed from energy waves detected, thereby to produce an IF signal useful for analysis in the frequency domain, and means for performing a further operation on the IF signal over the entire frequency spectrum of interest to produce a signal for display of amplitude or phase in the time domain.

13. Apparatus as defined in claim 12 wherein said means for performing said further operation comprises means for performing a fast Fourier transform operation on the IF signal over the entire frequency spectrum of interest to produce a signal representative of energy as a function of time during which said transmitted wave is swept for display as an energy-time curve, and means for displaying said energy-time curve.

14. Apparatus as defined in claim 13 wherein a path of interest through said medium has a uniform time delay, and said wave energy is produced through a transducer by a generated signal swept in frequency, including means for generating a selected second signal and means for mixing said generated signal with said second signal of a frequency selected to produce a signal to be transmitted that is offset in frequency from said swept generated signal sufficiently to offset said uniform time delay, thereby effectively displacing the frequency spectrum of said IF signal in time, and means for mixing said second signal with said IF signal to produce a second IF signal in which said offset is cancelled prior to said further operation.

15. Apparatus as defined in claim 14 including means for differentiating said IF signal prior to performing the fast Fourier transform operation in order to correct the energy-time curve data for inverse square loss in the medium due to spherical expansion of the wave energy transmitted through said medium.

16. Apparatus as defined in claim 15 including means for selecting the sum or difference frequency in the signal produced by said means for mixing said second signal with said IF signal to produce a second IF signal, and analog means for differentiating said second IF signal.

17. Apparatus as defined in claim 13 wherein a path of interest has a time delay that varies as a function of frequency or time, or a function of frequency and time, and said wave energy is produced through a transducer by a generated electrical signal swept in frequency over a predetermined time interval, including means for delaying said swept generated signal used to produce said IF signal with a delay time corresponding to time delay of energy wave transmission through said medium.

18. Apparatus as defined in claim 17 including means for mixing said IF signal with a signal from a local oscillator for analysis in the frequency domain.

19. Apparatus as defined in claim 17 or 18 including means for differentiating said IF signal prior to performing the fast Fourier transform operation in order to correct the energy-time curve data for inverse square loss in the medium due to spherical expansion of the wave energy transmitted through said medium.

20. Apparatus as defined in claim 19 wherein a path of interest through said medium has a uniform time delay, and said wave energy is produced through a transducer by a generated electrical signal swept in frequency, including means for mixing said generated electrical signal with a second signal of a frequency selected to produce a signal to be transmitted that is offset in frequency from said swept generated electrical signal sufficiently to offset said uniform time delay, thereby effectively displacing the frequency spectrum of said IF signal in time, and means for mixing said second signal with said IF signal to cancel said offset in said IF signal prior to said further operation.

21. Apparatus as defined in claim 20 including two frequency dividers and wherein said signal of selected frequency is generated by means for mixing said generated electrical signal swept in frequency with said second signal through said frequency dividers to divide equally the signals mixed by whole integers of 1, 2, 3 . . . N in order to produce said IF signal for analysis in the frequency domain and in the time domain as a function of harmonic frequency.

22. Apparatus as defined in claim 12 wherein said means for performing a further operation comprises means for mixing said IF signal with a fixed frequency, means for integrating the higher frequency signal, and means for displaying amplitude or phase in the time domain.

23. Apparatus as defined in claim 12 wherein a path of interest through said medium has a uniform time delay, and said wave energy is produced through a transducer by a generated electrical signal swept in frequency, including means for mixing said generated electrical signal with a second signal of a frequency selected to produce a signal to be transmitted that is offset in frequency from said swept generated electrical signal sufficiently to offset said uniform time delay, thereby effectively displacing the frequency spectrum of said IF signal in time, and means for mixing said second signal with said IF signal to cancel said offset in said IF signal prior to said further operation.

24. Apparatus as defined in claim 23 including two frequency dividers and wherein said signal of selected frequency is generated by means for mixing said generated electrical signal swept in frequency with said second signal through said frequency dividers to divide equally the signals mixed by whole integers of 1, 2, 3 . . . N in order to produce said IF signal for analysis in the frequency domain and in the time domain as a function of harmonic frequency.

* * * * *

UNITED STATES PATENT AND TRADEMARK OFFICE
CERTIFICATE OF CORRECTION

PATENT NO. : 4,279,019
DATED : July 14, 1981
INVENTOR(S) : Richard C. Heyser

It is certified that error appears in the above-identified patent and that said Letters Patent are hereby corrected as shown below:

Col. 2, line 64, the equation should be as follows:

$$h(t) = e^{i\phi(t)} = \cos\phi(t) + \sin\phi(t)$$

Col. 5, line 30, delete "fourier" and substitute -- Fourier --

Col. 8, line 33, "capacility" should be -- capability --

Claim 2, line 50, delete "total"

Claim 3, line 62, delete "frequecy" and substitute -- frequency --

Claim 9 should be as follows:

A method as defined in claim 1 wherein said further operation comprises mixing said IF signal with a fixed frequency, integrating the resulting signal, and displaying amplitude or phase in the time domain.

Signed and Sealed this

Fifteenth Day of December 1981

[SEAL]

Attest:

*Attesting Officer*

GERALD J. MOSSINGHOFF

*Commissioner of Patents and Trademarks*